Jan. 19, 1937. A. DICKSON, JR Plant Pat. 223
ROSE
Filed July 29, 1936
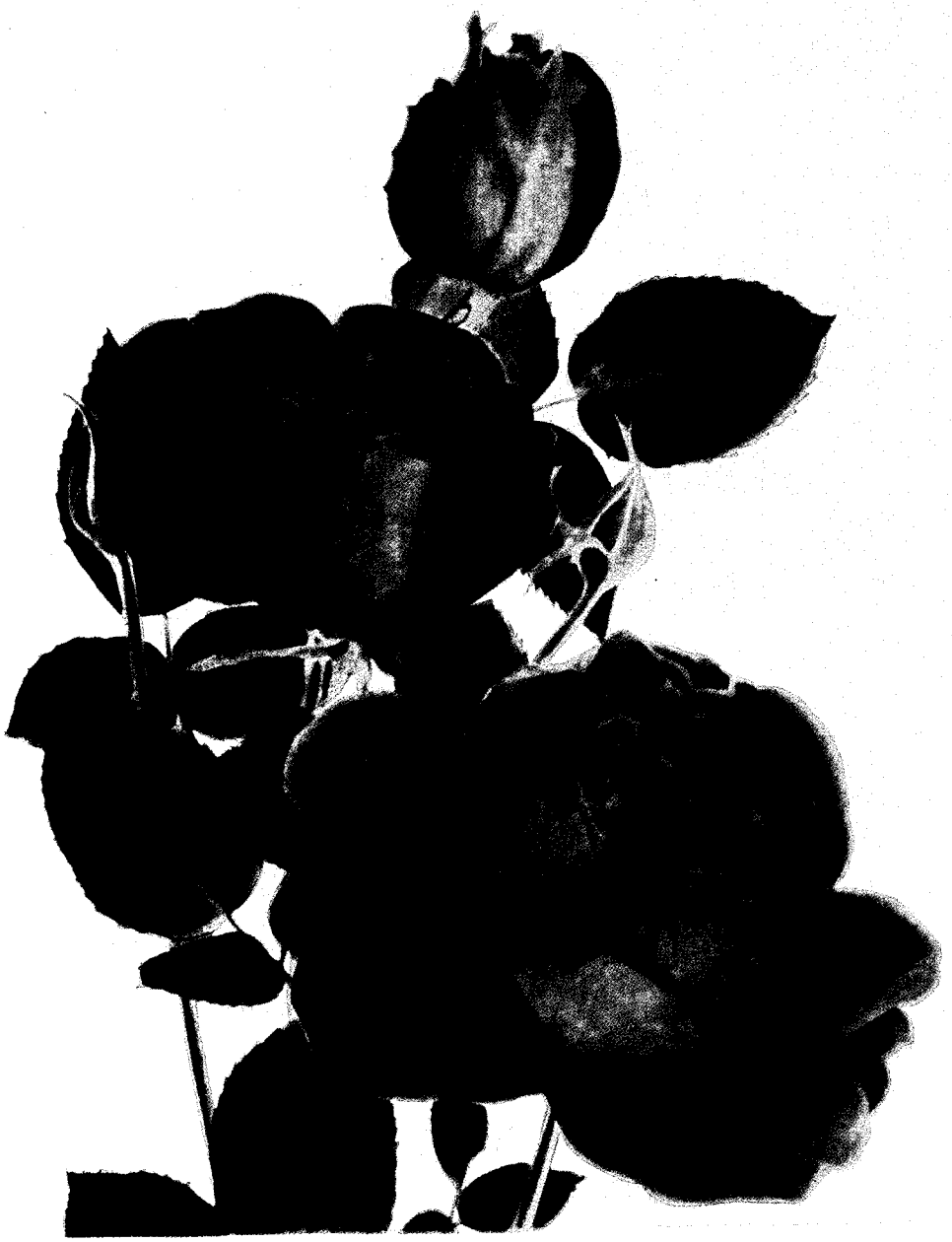
INVENTOR
Alex. Dickson Jr.
By Orville M Kile
Plant Patent Agent Patented Jan. 19, 1937

Plant Pat. 223

UNITED STATES PATENT OFFICE

223

ROSE

Alexander Dickson, Jr., Newtownards, near Belfast, Ireland, assignor to Henry A. Dreer, Incorporated, Philadelphia, Pa., a corporation of New Jersey Application July 29, 1936, Serial No. 93,288

1 Claim. (Cl. 47—61)

My invention relates to a new and distinct variety of rose plant of the hybrid tea class, the result of a definite effort to produce a dark red variety of vigorous growth and other desirable qualities. This variety is the result of a cross between two unnamed seedlings.

This variety is excellent for either greenhouse forcing or for a garden rose. One of the distinctive features of this rose is its peony-like appearance during the fall months—a feature not known by the inventor to exist in any other rose. The combination of its constant blooming habit and the very large flowers resembling a double peony makes it a very valuable fall blooming garden rose.

The original illustrations accompanying this application show in full color, buds and flowers in various stages of opening together with stems and foliage. It is to be understood, however, that the artist could not show with pigments the full brilliance and beauty of the flower.

Following is a detailed description of the rose plant, all color references being to Ridgway's Color Standards and Nomenclature.

*The plant*

Foliage:

*Leaflets.*—Usually five.

*Size.*—Medium.

*Quantity.*—Medium.

*Color.*—Upper side Forest Green (Plate XVII); under side Biscay Green (Plate XVII). Slight reddish tinge around edges and on petiole.

*Shape.*—Oval, pointed at apex.

*Texture.*—Substantial but not heavy.

*Edge.*—Serrated, small notches, sharp points.

*Rachis.*—Has one to three small thorns on under side.

*Arrangement.*—Leaflets have very short petioles, in many cases only $\frac{1}{16}$ of an inch or less.

*Stipules.*—Rather long and broad, terminating in non-curling points.

*Stems.*—Medium to short; strong.

*Wood.*—New wood reddish to bronze color.

*Thorns.*—Very numerous, large and strong; reddish in color; point downward very slightly; emanate from all sides.

*Disease resistance.*—Resists many diseases prevalent among roses.

*Frost resistance.*—Withstood severe winter when many other varieties were killed.

*The flower*

Blooming habit:

Free and constant blooming.

Borne:

Singly and in terminal groups of three to five.

Bud:

*Form.*—Ovoid.

*Color.*—Very dark—between Carmine and Oxblood Red (Plate I), with slight shadings of Amaranth Purple (Plate XII).

*Sepals.*—Rather short; non-foliaceous; have smooth edges; curl back before the bud fully opens.

*Peduncle.*—Short (about 2½ inches), heavy, reddish to brown, with small prickles.

Bloom:

*Size.*—Large to very large—usually 5 to 6 inches across.

*Form.*—Cupped, which form is retained to the end, with centre remaining unexposed. In the fall months the petals are incurved, making the bloom resemble a double peony.

*Petalage.*—Double, having in the month of May about 33 large heavy petals and 14 small central petals.

*Color.*—Between Carmine and Oxblood Red (Plate I). Rather uniform in color. Also the petals are velvety inside and have a brilliant shimmering effect that cannot be reproduced by the artist. Inside of petal is much more brilliant than outside. Each petal has a small white spot at point of attachment and most of the petals near the center of the flower have a narrow white streak up their middle—a prolongation of the white area at the point of attachment.

Petals:

*Form.*—Oval, slightly scalloped and crinkled at the upper middle edge.

*Arrangement.*—Imbricated.

*Fragrance.*—Mild.

*Genital organs*

*Stamens.*—Numerous, rather short, reddish colored, arranged in a distinct ring, topped with light brownish colored anthers of medium size.

*Pistils.*—Slightly longer and located much higher than the stamens; reddish in color with grayish tops.

*Ovaries.*—Surrounded by unusually large amount of pithy substance, which tends to give size to the flower.

Having thus disclosed my invention, I claim:

A new and distinct variety of rose plant as shown and described, characterized particularly by the distinctive dark red coloring and peony-like form of its fall blossoms, in combination with its vigorous growth and free blooming habits.

ALEX. DICKSON, Jr.